US006403835B1

(12) United States Patent
Davis et al.

(10) Patent No.: US 6,403,835 B1
(45) Date of Patent: Jun. 11, 2002

(54) ACYLATION OF AN ORGANIC GROUP OVER A ZEOLITE

(75) Inventors: Mark E. Davis, Pasadena, CA (US); Patricia Andy, Mandelieu (FR); Javier Garcia Martinez, Alicante (ES); Gary Lee, Albany; Hector Gonzalez, San Francisco, both of CA (US); Christopher W. Jones, Smyrna, GA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/705,060

(22) Filed: Nov. 2, 2000

Related U.S. Application Data

(60) Provisional application No. 60/163,234, filed on Nov. 2, 1999.

(51) Int. Cl.[7] ........................... C07C 45/29; C07C 45/46
(52) U.S. Cl. .................. 568/309; 568/338; 568/38; 568/44; 544/128; 544/135; 544/146
(58) Field of Search ................................ 568/309, 338, 568/44, 38; 544/128, 135, 146

(56) References Cited

U.S. PATENT DOCUMENTS

| | | | |
|---|---|---|---|
| 5,164,527 A | * 11/1992 | Newton | |
| 5,817,878 A | * 10/1998 | Spagnol et al. | |
| 6,084,096 A | 7/2000 | Li et al. | 544/352 |
| 6,117,411 A | 9/2000 | Takewaki et al. | 423/705 |
| 6,121,496 A | 9/2000 | Gilbert et al. | 568/42 |

OTHER PUBLICATIONS

P. Andy et al., Acylation of 2–Methoxynaphthalene and Isobutylbenzene over Zoelite Beta, Journal of Catalysis 192, Feb. 18, 2000, pp. 215–223.
S. Kim et al., The Regioselective Acylation of 2–Methoxynaphthalene to 2–Acetyl–6–Methoxynaphthalene over Zeolite Beta, Journal of Molecular Catalysis A: Chemical 152, Jun. 22, 1999, pp. 33–45.
D. Rohan et al., Origin of the Deactivation of HBEA Zeolites During the Acylation of Phenol with Phenylacetate, Journal of Molecular Catalysis A: Chemical Jun. 21, 1997, pp. 69–78.
F. Jayat et al., Acylation of Aromatics over a HBEA Zeolite. Effect of Solvent and of Acylating Agent, Heterogeneous Catalysis and Fine Chemicals IV, 1997, pp. 91–98.
K. Smith et al., Zeolite–Catalysed Acetylation of Alkenes with Acetic Anydride, Heterogeneous Catalysis and Fine Chemicals IV, 1997, pp. 99–106.
E. Fromentin et al., Mechanism of 1–Acetyl–2–Methoxynaphthalene Isomerisation over a HBEA Zeolite, Journal of Catalysis 190, Nov. 12, 1999, pp. 433–438.
P. Moreau et al., Liquid–Phase Acetylation of Tetralin with Acetyl Chloride over Zeolites: Inhibition of the Reaction by the Products, Catalysis Letters 47, Jun. 30, 1997, pp. 161–166.
D. Rohan et al., Acetylation of Anisole by Acetic Anhydride over a HBEA Zeolite–Origin of Deactivation of the Catalyst, Journal of Catalysts 177, Apr. 17, 1998, pp. 296–305.
I. Neves et al., Phenol Acylation: Unexpected Improvement of the Selectively to O–Hydroxyacetophenone by Passivation of the External Acid Sites of HZSM5, J. Chem. Soc., Chem. Commun., vol. 6, 1994, pp. 717–718.
F. Jayat et al., Acylation of Phenol with Acetid Acid. Effect of Density and Strength of Acid Sites on the Properties of MFI Metallosilicates, Stud. Surf. Sci. Catal. 105B, 1997, (Progress in Zeolite and Microporous Materials, Pt. B.) pp. 1149–1156 (Abstract).

* cited by examiner

*Primary Examiner*—Sreeni Padmanabhan
*Assistant Examiner*—Sikarl A. Witherspoon
(74) *Attorney, Agent, or Firm*—Pillsbury Winthrop LLP

(57) ABSTRACT

The invention relates to the shape selective acylation of an organic compound. In particular, the invention describes a process for such acylation wherein the process comprises reducing the number of surface acid sites without dealuminations on at least a portion of the surface of a zeolite and acylating the organic compound in the presence of the zeolite. The organic compounds used in the invention include, for example, olefins, aromatic hydrocarbons, aromatic heterocyclic compounds, and phenolic compounds wherein the organic group may be substituted or unsubstituted. The zeolite may be any natural or synthetic zeolite with a unidimensional or multidimensional network, for example a two-dimensional, or three-dimensional network, or any molecular sieve with structural features similar to these.

26 Claims, 4 Drawing Sheets

ACYLATION OF AN ORGANIC GROUP OVER A ZEOLITE

The present application claims the benefit of U.S. Provisional Application No. 60/163,234, filed Nov. 2, 1999, by inventor Mark E. Davis entitled ACYLATION OF 2-METHOXYNAPHTHALENE AND ISOBUTYLBENZENE OVER ZEOLITE BETA, the contents of which are incorporated herein by reference in their entirety.

BACKGROUND

Acylation is a key step in the manufacture of intermediates in the fine chemical and pharmaceutical industry. The Friedel Craft acylation is a step that can be used in the production of such pharmaceutical compounds as (S)-naproxen (1) and ibuprofen (2).

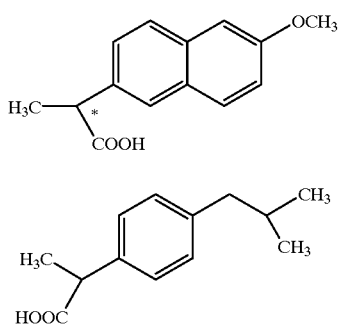

For example, the acylation of 2-methoxynaphthalene (2 MN) in the presence of aluminum chloride was a step in the first large-scale synthesis of naproxen and the acylation of isobutylbenzene with hydrogen fluoride as catalyst is currently used in the synthesis of ibuprofen. Because of current environmental restrictions, replacement of conventional homogeneous catalysts with solid acid catalysts has great industrial importance. Zeolites, with their shape selective properties and good regenerability, have been found to be viable alternatives to liquid acids in numerous cases. A recent study shows the first industrial application of a zeolite promoted acylation for the production of an aromatic ketone.

The acetylation of 2 MN has been investigated over MCM-41, HY, ZSM-12 and *BEA, and ZSM-5 and mordenite. Two products are usually obtained, 1-acetyl-2-methoxynaphthalene (1,2-AMN and 2-acetyl-6 methoxynaphthalene (2,6-AMN), with the undesired 1,2-AMN product generally predominating. Indeed, the acylation generally occurs at the kinetically favored 1-position. However, the deacylation of the acyl group has been observed to give back 2MN. These results are consistent with the following reaction as shown in Scheme 1:

SCHEME 1

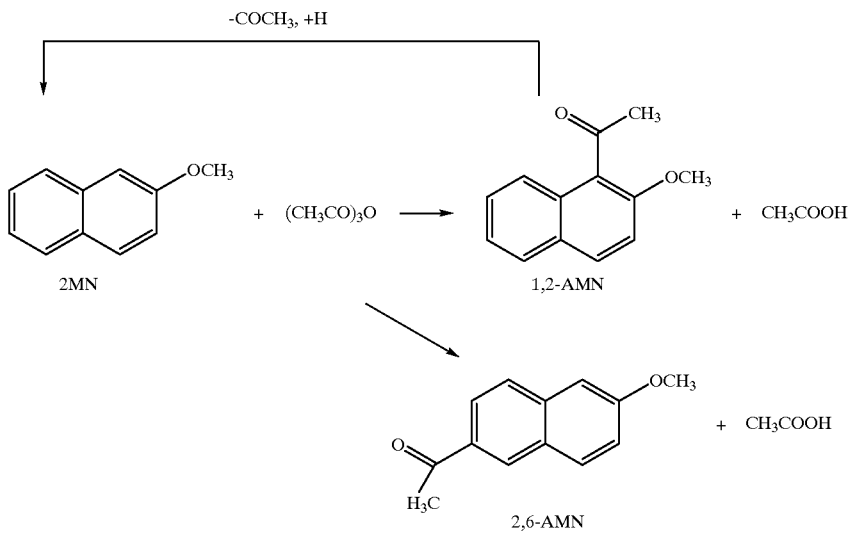

It would therefore be advantageous to identify materials and methods that can be used to improve the yield of desired organic groups in acylation reactions, particularly those catalyzed using zeolite beta. This would be particularly useful in the pharmaceutical industry as it would provide a viable acylation catalyst for the formation of precursors to, for example, the nonsteroidal anti-inflammatory agent, naproxen.

SUMMARY

This invention comprises a process for the shape selective acylation of an organic compound, the process comprising the steps of reducing the number of surface acid sites on at least a portion of the surface of a zeolite, and acylating the organic compound in the presence of the zeolite. The organic compounds include, for example, olefins, aromatic hydrocarbons, phenolic compounds, and heterocyclic compounds, wherein the organic group may be substituted or unsubstituted. The zeolite may be any synthetic zeolite with a unidimensional, two-dimensional, or three-dimensional network, or any molecular sieve with structural features similar to these. The acylation may occur in the presence of an acylating agent. Such acylating agents include, for example, halides of aliphatic carboxylic acids and the anhydrides of carboxylic acids.

BRIEF DESCRIPTION OF THE DRAWINGS

The ivention will be better understood by reference to the attached figures in which.

DETAILED DESCRIPTION

Figure 1:
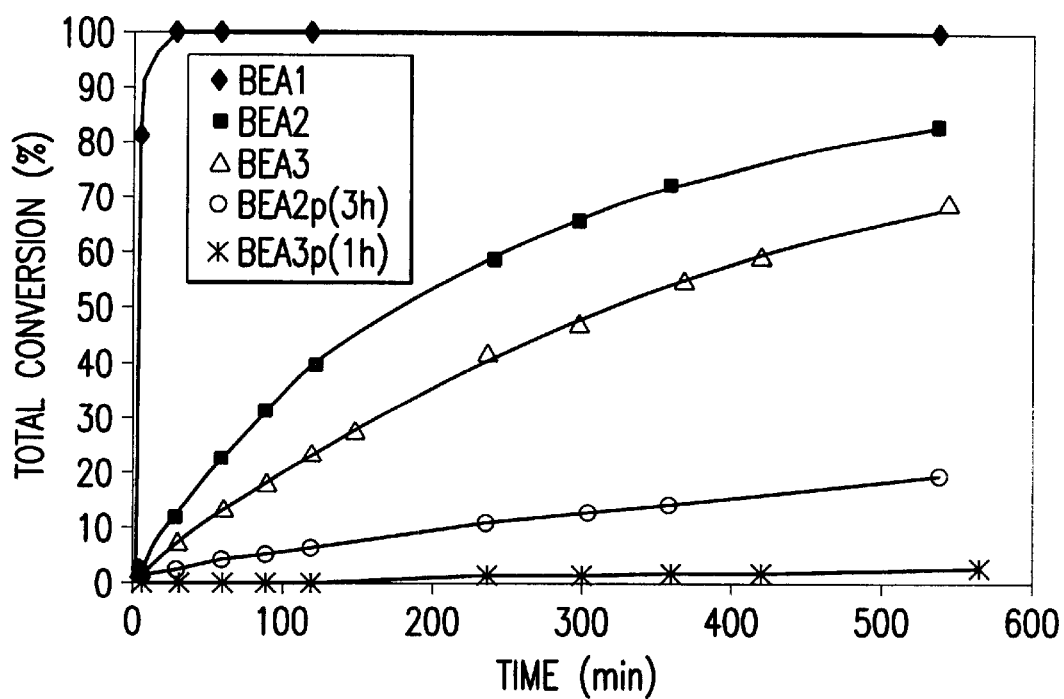
FIG. 1 shows the conversion of allyl 3-5-di-tert-butylphenyl ether versus reaction time over zeolite beta samples.

The invention relates to the shape selective acylation of an organic compound. In particular, the invention is a process for such acylation wherein the process comprises reducing the number of surface acid sites on at least a portion of the surface of a zeolite, and acylating the organic compound in the presence of the zeolite. The organic compounds used in the invention include, for example, olefins, aromatic hydrocarbons, aromatic heterocyclic compounds, and phenolic compounds wherein the organic group may be substituted or unsubstituted. The aromatic hydrocarbons may be any single ring or polycyclic compound capable of electrophilic aromatic substitution. Such compounds include, for example, toluene, styrene, cumene, naphthalene, 2-methoxynaphthalene, phenanthrene, anthracene, biphenyl, chrysene, pyrene, coronene and tetralin. Similarly, the aromatic heterocyclic compounds may be any heterocyclic compound capable of electrophilic aromatic substitution. Such aromatic heterocyclic compounds include nitrogen heterocycles such as, pyridine, pyrimidine, quinoline, isoquinoline, purine, pyrrole, thiazole, oxazole, pyrazole, imidazole, and indole; furan and benzofuran; and thiophene and benzothiophene. The phenolic compounds include, for example, phenols, cresols, hydroxyphenols and anisoles. The organic group may optionally be substituted with one or more moieties selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein the moiety may be substituted or unsubstituted. The moiety substitution may be any member selected from the group consisting of $C_1$–$C_5$ alkyl, $C_1$–$C_5$ alkoxy, and phenyl. The organic group may also be functionalized with a moiety selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The zeolite may be any natural or synthetic zeolite with a unidimensional or multidimensional network, for example a two-dimensional, or three-dimensional network, or any molecular sieve with structural features similar to these. Zeolites of the aluminosilicate type are the most common. Examples of natural zeolites include chabazite, clinoptilolite, erionite, phillipsite, and offretite. Preferably, however, synthetic zeolites are used in the inventive process. Examples of synthetic zeolites with a unidimensional network include zeolite ZSM-12, zeolite ZSM-22, zeolite ZSM-23, zeolite ZSM-48, VPI-8, VPI-5, SAPO-5, SAPO-11, SSZ-31, and theta-1. Examples of synthetic zeolites with a two-dimensional or three dimensional network include mordenite, ferrierite, SSZ-36, SSZ-35, gmelinite, NU-87, zeolite beta, zeolite Y, zeolite X, zeolite ZSM-5, zeolite ZSM-11, zeolite ZSM-4, zeolite L, SAPO-34, Rho, zeolite A, CIT-1, SSZ-33, SSZ-26, SSZ-16, SSZ-13, zeolite ZSM-18, and zeolite HY. The zeolites may be synthesized according to known processes; however, commercially available zeolites may also be used. Preferably the zeolite is SSZ-33 or zeolite beta.

The zeolites may have different Si/Al ratios and crystal sizes depending upon the zeolite used. For example, mazzite may have an Si/Al molar ratio of 3.4; zeolite L with an Si/Al molar ratio of 1.5 to 3.5; mordenite with an Si/Al molar ratio of 5 to 150, preferably 10 to 100 and even more preferably 10 to 25; fenrierite with an Si/Al molar ratio of 3 to 10; offretite with an Si/Al ratio of 4 to 8.5; zeolite beta with an Si/Al molar ratio greater than 8, preferably between 10 and 40, and even more preferably between 12 and 40; zeolite Y with an Si/Al molar ratio greater than 3, preferably between 6 and 60; zeolite X with an Si/Al molar ratio of 0.7 to 1.5; zeolite ZSM-5 or aluminum silicate with an Si/Al molar ratio of 10 to 500; and zeolite ZSM-11 with an Si/Al molar ratio of 5 to 30.

The surface of zeolite may be modified by any method which reduces the number of surface acid sites. Surface poisoning and surface passivating are two examples of methods which reduce the surface acid sites on the zeolite. Surface poisoning occurs in the presence of for example, 2,4,6-tri-tert-butylpyridine and triphenylphosphine. With regard to the surface passivation treatment, the surface may be passivated by coating the surface with silica. Useful passivating agents include silicon-containing materials capable of passivating the surface of a crystalline aluminosilicate. Examples of silicon-containing passivating agents for use in the passivation treatment include tetraalkoxysilanes, also known as tetraalkyl orthosilicates, such as tetramethoxysilane and tetraethoxysilane, dimer to hexamer of tetraalkoxysilanes, silicon tetrachloride, dimethyldichlorosilane, trimethylchlorosilane, tetramethyldisilazane and hexamethyldisilazane.

The organic compound is acylated in the presence of the zeolite. The acylation reaction is preferably carried out using an acylating agent with or without a solvent. The acylating agent may be selected from the group consisting of halides of carboxylic acids and the anhydrides of carboxylic acids. The carboxylic acids may be saturated or unsaturated, linear or branched aliphatic carboxylic acids or substituted or unsubstituted, saturated or unsaturated cycloaliphatic acids. Example substituents include $C_1$–$C_6$ alkyl, $C_1$–$C_6$ alkoxy, or a halogen. The preferred acylating agent is acid anhydride. Examples of acid halide acylating agents include acetic anhydride, propanoic anhydride, isobutyric anhydride, trifluoroacetic anhydride, trichloroacetic anhydride, monochloroacetyl anhydride, monochloroacetyl anhydride, acetyl chloride, monochloroacetyl chloride, dichloroacetyl chloride, propanoyl chloride, isobutanoyl chloride, pivaloyl chloride, and crotonyl chloride.

The reaction may take place in the presence or absence of a solvent. Examples of suitable solvents include aliphatic or aromatic, halogenated or non-halogenated aliphatic hydrocarbons, aliphatic, cycloaliphatic or aromatic ether oxides. Aliphatic hydrocarbons include the paraffins, for example, hexane, heptane, octane, nonane, decane, undecane, dodecane, tetradecane, and cyclohexane. Aromatic hydrocarbons include, for example, naphthalene, benzene, toluene, xylenes, and cumene.

Aliphatic or aromatic halogenated hydrocarbons include, for example, perchlorinated hydrocarbons such as, for example, tetrachloroethylene, hexachloroethane, partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane, monochlorobenzene, 1,2-dichlorobenzene, 1,3-dichlorobenzene, 1,4-dichlorobenzene, 1,2,4-trichlorobenzene or mixtures of different chlorobenzenes; bromoform, bromoethane or 1,2-dibromoethane; monobromobenzene or mixtures of monobromobenzene with one or more dibromobenzenes; and 1-bromonaphthalene.

Organic solvents that may also be used include aliphatic, cycloaliphatic or aromatic ether oxides and more preferably, diethyl oxide, dipropyl oxide, diisopropyl oxide, dibutyl oxide, methyltertiobutylether, dipentyl oxide, diisopentyl oxide, the dimethylether of ethylene glycol (or 1,2-dimethoxyethane), the dimethyl ether of diethylene glycol (or 1,5-dimethoxy 3-oxapentane); benzyl oxide, dioxane, and tetrahydrofuran. More polar organic aprotic solvents that may be used in the invention include nitrated compounds, for example, nitromethane, nitroethane, 1-nitropropane, 2-nitropropane or mixtures thereof, nitrobenzene; aliphatic or aromatic nitrites such as acetonitrile, proprionitrile, butane nitrile, isobutane nitrile, benzonitrile, benzyl cyanide, linear or cyclic carboxamides such as N,N-dimethylacetamide, N,N-diethylacetamide, dimethylformamide, diethylformamide and 1-methyl-2-pyrrolidinone; dimethylsulphoxide, tetramethylene sulphone (sulpholane), and hexamethylphosphotriamide. The solvent may also be a mixture of any of the organic solvents. Preferably the solvent is selected from the group consisting of dichloromethane, dichloroethane, tetrachloromethane, tetrahydrofuran, and diethyl oxide. Most preferably, the solvent is dichloroethane. In addition, the solvent may serve as the organic compound reaction substrate.

The acylation of 2-MN over zeolite beta is preferred. The results from all previous investigations suggest that zeolite beta may be the most interesting catalyst for the production of 2,6-AMN since it was speculated that its formation is favored inside the 12 membered channel of *BEA. However, due to the contribution of acid sites on the external surface of the crystals, a large amount of 1,2-AMN product is formed. Upon the acylation of 2MN with zeolite beta, it was determined that the external surface sites of the zeolite can be eliminated in order to improve the performance of the catalyst. This is surprising as it has been thought that the external surface plays an important role in the catalytic activity.

Different Si/Al ratio and crystal sizes may be used. Table 1 lists the Si/Al ratio as determined by elemental analysis and the crystal size of examples of preferred zeolite beta samples BEA1, BEA2 and BEA3 as determined by SEM. Materials that are synthesized in fluoride media such as BEA2 and BEA3 have larger crystal sizes than the commercial sample. BEA2, obtained under stirred conditions has smaller crystal size than BEA3 that was prepared at static conditions. All of these samples have a XRD pattern typical of highly crystalline *BEA.

TABLE 1

| Sample | Si/Al | Crystal size ($\mu$m) |
|---|---|---|
| BEA(1) | 12 | >1 |
| BEA(2) | 40 | 2.5 |
| BEA(3) | 40 | 9 |

The micropore volume of the parent zeolites BEA1, BEA2 and BEA3 and the passivated samples BEA1p(3h), BEA2p(3h) and BEA3p(3h) (as prepared in Example 2) are given in Table 2. Except for BEA1, the micropore volumes determined with nitrogen and cyclohexane are similar. From the nitrogen adsorption isotherm of small zeolite beta crystals it is impossible to know where the onset of extracrystalline adsorption occurs. Thus, for the case of BEA1, it is likely the volume determined with nitrogen is slightly overestimated as it takes also account of a part of the extracrystalline volume of this zeolite. Thus, the cyclohexane adsorption values are the most reliable and show that no decrease in the pore opening of the passivated zeolites occurs as they have the same micropore volume as the parent zeolites. The coincidence of micropore volume of the unpassivated and passivated samples suggests that there is not a significant blockage of the pore opening when the zeolites are passivated. This is true not only for a small molecule such as nitrogen but also for a larger molecule such as cyclohexane.

TABLE 2

| | Micropore volume ($cm^3/g$) | |
|---|---|---|
| Sample | Nitrogen adsorption | Cyclohexane adsorption |
| BEA1 | 0.24 | 0.20 |
| BEA2 | 0.19 | 0.21 |
| BEA3 | 0.19 | 0.22 |
| BEA1p(3h) | 0.20 | 0.22 |
| BEA2p(3h) | 0.18 | 0.21 |
| BEA3p(3h) | 0.18 | 0.22 |

FIG. 1 shows the total conversion of allyl 3-5-di-tert-butylphenyl ether over zeolite beta samples. In particular, FIG. 1 shows the conversion of allyl 3-5-di-tert-butylphenyl ether versus reaction time over BEA1, BEA2, BEA3, BEA2p(3h) and BEA3p(1h) using 0.10 g of catalyst at 100° C., 0.4 nunol of allyl 3-5-di-tert-butylphenyl ether in 2 mL of 1,2-dichloroethane.

The conversion of the probe molecule is significantly higher on zeolite BEA1 with small crystals than on BEA2 and BEA3 (BEA2 and BEA3have larger crystals and thus less acid sites on external surface than BEAL). Moreover the conversion is lower on the passivated samnples BEA2p(3h) and BEA3p(1h) than on the parent zeolites BEA2 and BEA3. This result shows that the coating of zeolite with medium crystal size and in particular big crystal size is very efficient. Almost all the acid sites on the external surface are covered by the amorphous silica layer.

Figure 2A:
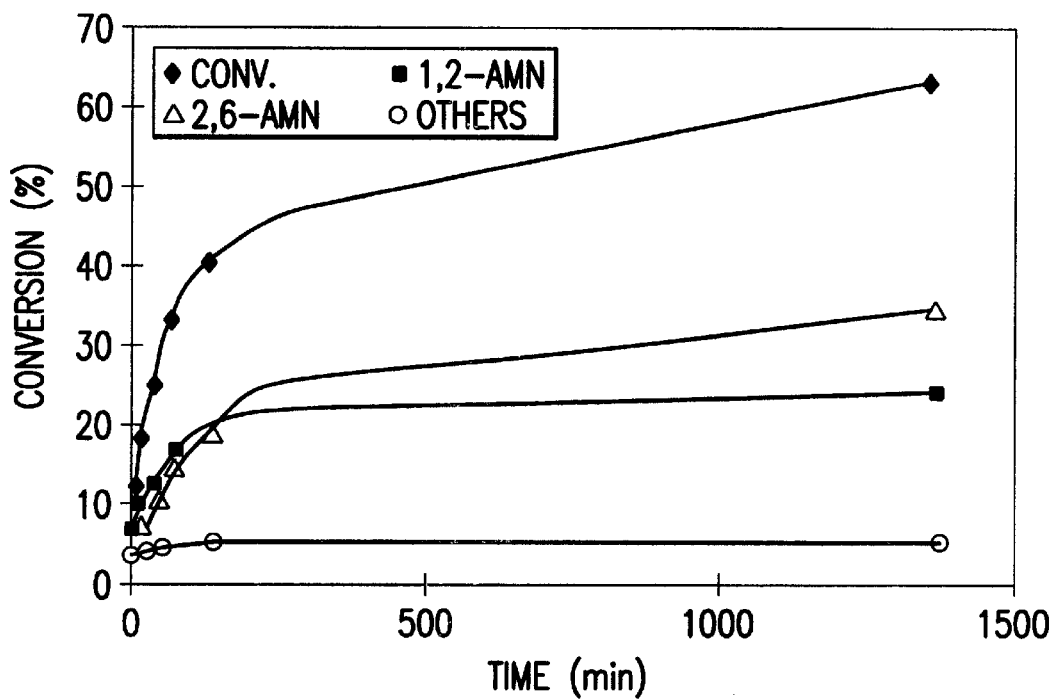
FIG. 2a shows the conversion of 2MN versus reaction time over zeolite BEA1.
Figure 2B:
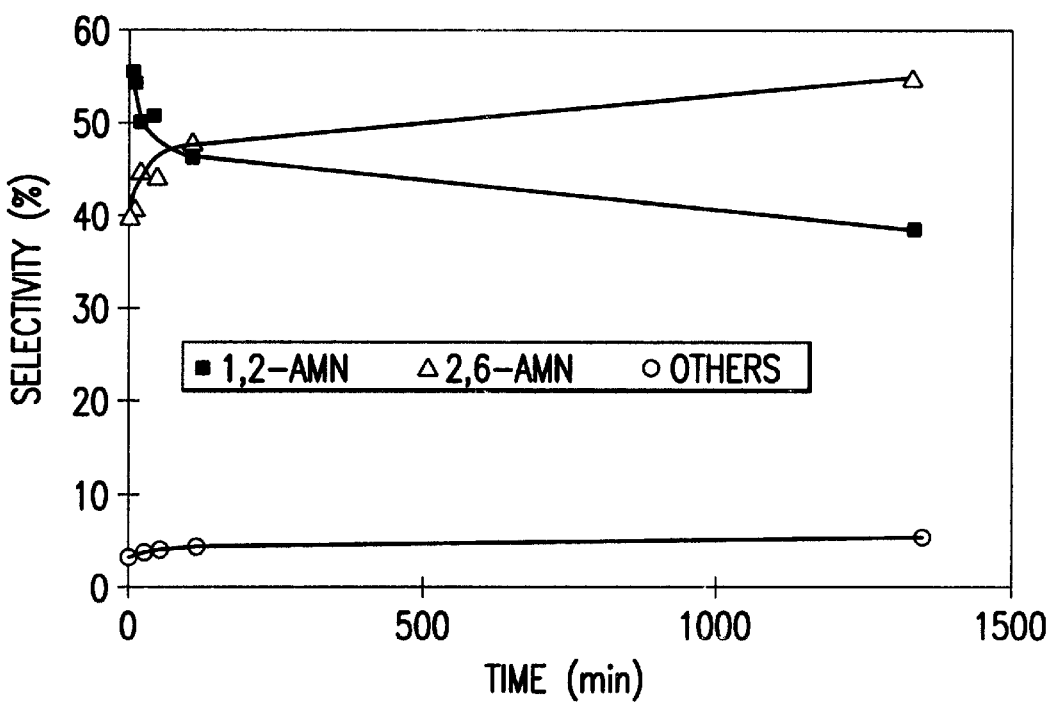
FIG. 2b shows the selectivity of acylated products versus reaction time over zeolite BEA1.

In the acylation of 2MN with acetic anhydride over zeolite beta, the operating conditions may also contribute to the formation of 2,6-AMN. For example, FIG. 2a shows the total conversion of 2MN and the yield of reaction products versus reaction time over zeolite BEA1. In particular, FIG. 2a shows the conversion of 2MN versus reaction time over zeolite BEA1 using 0.10 g of catalyst at 100° C. wherein the ratio of 2MN to acetic anhydride is 1:1 and 1.1 mmol, in 0.860 mL of solvent. 2MN is mainly transformed into 1,2-AMN and 2,6-AMN. Small amounts of the other monoacylated methoxynaphthalene isomers are produced. As the reaction progresses, traces of diacylated compound are formed. The conversion of 2MN is 39% at 2h and then slowly levels off to a final value of 62% at 24h. Initially 1,2-AMN is formed with a slight selectivity over 2,6-AMN. FIG. 2b shows the selectivity of acylated products versus reaction time over zeolite BEA1 using 0.10 g of catalyst at 1 00° C. wherein the ratio of 2MN to acetic anhydride is 1:1 and 1.1 mmol, in 0.860 mL of solvent. With longer reaction times, the opposite selectivity is observed as shown in FIG. 2b.

The weight of the catalyst may also contribute to the formation of 2,6-AMN. The reaction was conducted at four different weights of catalyst from 30 mg to 140 mg. The increases in conversion of 2MN and yields of 1,2-AMN and 2,6-AMN (at 4min of reaction) are linear when the weight is increased from 30 mg to 100 mg. Above this weight, the conversions no longer increase catalyst mass. Also, the initial selectivity for 2,6-AMN is higher when the zeolite weight decreases. However, after 24h of reaction, the selectivity is independent of the weight of the catalyst.

The reaction was also conducted at various temperatures, for example at 70° C., 100° C. and 120° C. The yield and the selectivity of 2,6-AMN increase significantly when the temperature increases. The yield of 1,2-AMN increases when the temperature is elevated from 70° C. to 100° C. However, at 120° C., a decrease in the yield of 1,2-AMN is observed with reaction time and may be due to the protiodeacylation of the acyl group. The increase in the temperature leads also to catalyst samples becoming more dark in color after reaction and likely indicate increasing carbonaceous residues content. In addition, the apparent activation energies are estimated to be 21 Kj/mol for 1,2-AMN and 45 Kj/mol for 2,6-AMN.

Preferably, acetic anhydride is used as an acylating agent. The ratio of acetic anhydride to 2MN was also varied while maintaining the amount of 2MN and the total volume constant. At early reaction times, the concentration of the acylating agent has practically no influence on the conversion of 1,2-AMN and 2,6-AMN: thus, the reaction order is close to 0 order. At longer reaction times, the effect of the ratio of acetic anhydride to 2MN is different for the formation of 1,2-AMN and 2,6-AMN. At longer reaction times, the kinetic product (1,2-AMN) is favored when the ratio of $Ac_2O$/2MN increases, whereas the conversion to 2,6-AMN is a maximum for a ratio equal to 2. Moreover, it must be noted that in the presence of an excess of acylating agent (2MN/acetic anhydride >1), small amounts of diacylated compounds are formed and the catalyst rapidly turns into a dark solid that is indicative of large formation of heavy products (increase in catalyst weight after 24h of reaction is 11.7% as opposed to 7.6% at a ratio of 1). Finally, in the presence of acylating agent a slight dealumination of the zeolite is observed: before reaction the Si/Al ratio is equal to 12, after 24h of reaction the Si/Al ratio is equal to 14.2 and 16.3 for a ratio of acetic anhydride to 2MN equal to 1 and 4 respectively.

Moreover, the addition of acetic acid (2MN/acetic anhydride/acetic acid =1) leads to a significant decrease in the yield of 1,2-AMN and 2,6-AMN but a small increase in the selectivity of 2,6-AMN. Moreover, the increase in weight of the catalyst after 24h of reaction is higher in presence of acetic acid (10.3% instead of 7.1%). This could be due to a strong adsorption of acetic acid on the internal and external sites of the zeolite.

Deacylation experiments with 1,2-AMN and 2,6-AMN were also carried out during 2h at 100° C. in dichloroethane in presence of acetic acid (AMN/acetic acid=1). Table 3 shows the conversion of 1,2-ANN and 2,6-AMN over zeolite BEA1. For reactions 1 and 3, 0.10 g of catalyst was used at 100° C. for 2h. The ratio of 1,2-AMN (or 2,6-AMN) to acetic acid was 1:1 and 1.1 mmol in 0.860 Ml of solvent. For reaction 2, 0.10 g of catalyst was used at 100° C. for 2h. The ratio of 1,2-AMN to acetic anhydride to acetic acid was 1:1:1 and 1.1 mmol in 0.860 Ml of solvent. The deacylation of 1,2-AMN leads to the formation of 2MN (19.2%) and 2,6-AMN (0.6%). However, the protiodeacylation of the acyl group at the 1-position is limited in presence of acetic anhydride (1,2-AMN/acetic acid/acetic anhydride=1). The deacylation reaction eventually does not occur with the thermodynamically more stable 2,6-AMN.

TABLE 3

| No. | Reactant | Conv. (%) | 2MN (%) | 1,2-AMN (%) | 2,6-AMN (%) |
|---|---|---|---|---|---|
| 1 | 1,2-AMN | 19.8 | 19.2 | — | 0.6 |
| 2 | 1,2-AMN | 5.1 | 4.2 | — | 0.5 |
| 3 | 2,6-AMN | 0.3 | 0.2 | 0.1 | — |

Deacylation experiments with 1,2-AMN and 2,6-AMN in absence of acylating agent were also carried out at 100° C. in dichloroethane. After 2h, no reaction of AMN is observed. However, after 24h, 44% of 1,2-AMN is transformed and gives 20.8% of 2MN and 19.2% of 2,6-AMN whereas no transformation of 2,6-AMN is observed at the same conditions. These results show that 1,2-AMN is deacylated to give back 2MN which then, can be acylated again to form 2,6-AMN, the thermodynamic product.

The composition of carbonaceous residue was also determined on 400 rng of a sample exposed to the reaction at 100° C. for 24h. A large part of the retained compounds are extracted in methylene chloride by simple soxhlet treatment of the sample (5.6 wt. % of the catalyst) which means that the reaction occurs mainly close to the external surface rather than in the heart of the crystallite. The extract contains mainly 2,6-AMN and diacylated products that are not observed in the reaction solution. Table 4 shows the composition of the organic compounds retained on the zeolite BEA1. The wt(%) is the weight percentage of extract on the catalyst. Row 1 shows the weight percentage before extraction whereas Row 2 shows the weight percentage after extraction. Moreover, the 2,6-AMN to 1,2-AMN ratio is higher in the extract (2.3) than in the reaction solution (1.5).

TABLE 4

| | | Distribution (%) | | | |
|---|---|---|---|---|---|
| Wt (%) | 2MN | 1,2-AMN | 2,6-AMN | others AMN | di-AMN |
| 1 5.6 | 9 | 18 | 41 | 4 | 28 |
| 2 0.7 | — | — | trace | — | >95 |

A less significant part of the retained compounds are not collected by extraction and can be recovered in a hydrofluoric acid solution that dissolves the zeolite. As can be seen in Table 4, more than 95% of the compounds are diacylated molecules that may be formed by acylation of 2,6-AMN.

Contribution of the External Surface

The transformation of 2MN, for example, was carried out in presence of 2,4,6-tri-tert-butylpyridine (5 mol % of 2MN) or triphenylphosphine (5 wt. % of catalyst) for 2h on the zeolite with small crystal size and high surface area, BEA1. These molecules are too large to be accommodated inside the zeolite pores and can be adsorbed on the external acid sites. In absence of poison, the total conversion is equal to 39.2% and the selectivity to 2,6-AMN is equal to 48%. In presence of poison, a significant decrease in the total conversion occurs (the conversion is equal to 7.5% in presence of 2,4,6-tri-tert-butylpyridine and to 42% in presence of triphenylphosphine) but an increase in the selectivity of 2,6-AMN is observed (75% in presence of 2,4,6-tri-tert-butylpyridine and 61% in presence of triphenylphosphine). This suggests that a large amount of 1,2-AMN is formed on the external surface and that the selective acylation of 2MN into 2,6-AMN occurs inside the zeolite pores.

Three zeolite beta samples with varying crystal size were studied to determine the effect of crystal size for the acylation of 2MN: BEA1 with small crystal size, BEA2 with intermediate crystal size and BEA3 with large crystals. BEA1 has a Si/Al equal to 12 and BEA2 and BEA3 both equal to 40, as shown in Table 1.

The total conversion of 2MN is quite the same on BEA1, BEA2 and BEA3. This would suggest that the reaction occurs close to the external surface of the zeolite. The yield of 1,2-AMN is higher for the zeolite with the lower Si/Al ratio and the smaller crystals while the yield of 2,6-AMN is higher on the zeolites with larger crystal size (BEA2 and BEA3). The suggests that the shape selective acylation on 6-position occurs preferentially in the interior of the crystals as the relative number of external acid sites are decreased with increasing crystal size. To test this premise corroborated by the poisoning experiments, attempts to passivate the external crystal surfaces were explored.

The activity and selectivity of the passivated zeolite beta samples BEA1p(3h), BEA2p(3h) and BEA3p(3h) are compared to those of the parent zeolites BEA1, BEA2 and BEA3. Table 5 shows the acylation of 2MN catalyzed by zeolite beta samples. The effect of surface modification on reaction behavior are given. The reaction used 0.10 g of catalyst at 100° C. for 2h. The ratio of 2MN to acetic anhydride was 1:1 and 1.1 mmol in 0.860 Ml of solvent. data in row 4 were obtained at 30 minutes of reaction and the data in row 7 were at 4 minutes of reaction.

TABLE 5

| No. | Sample | Conv. (%) | Yield of 1,2- | Yield of 2,6-AMN (%) | Yield of other AMN (%) | Selectivity of 2,6-AMN (%) |
|---|---|---|---|---|---|---|
| 1 | BEA1 | 39.2 | 18.5 | 18.8 | 1.9 | 48 |
| 2 | BEA1p(3h) | 36.8 | 15.7 | 19.2 | 1.9 | 52 |
| 3 | BEA2 | 46.8 | 17 | 27.4 | 2.1 | 58 |
| 4 | BEA2 | 30.9 | 12.2 | 17.4 | 1.2 | 56 |
| 5 | BEA2p(3h) | 23.6 | 5.7 | 16.8 | 1.1 | 71 |
| 6 | BEA3 | 35.5 | 12.1 | 21.5 | 1.7 | 60 |
| 7 | BEA3 | 6.3 | 2.6 | 3.4 | 0.2 | 55 |
| 8 | BEA3p(3h) | 8.5 | 0.4 | 7.9 | 0.2 | 92 |

As shown in Table 5, compared to the parent zeolites, the passivation of the external surface by coating the crystal with amorphous silica leads, after 2h of reaction, to a decrease in the conversion but an increase in the selectivity of 2,6-AMN. This phenomena is more pronounced as the size of the crystal increases. Table 5 also shows the results from passivated and nonpassivated BEA2 and BEA3 at similar conversions in order to compare their activities in similar conditions. At near isoconversion, the yield of 2,6-AMN is higher on BEA3p(3h) (7.9%) than on BEA3 (3.4%) and the yield of 1,2-AMN is dramatically suppressed on the passivated sample.

FIG. 1 shows that the coverage of the external surface by amorphous silica is significantly better on larger crystals. Moreover, XPS analysis shows that the Si/Al of BEA3 increases from 37 to 62 after the passivation treatment. These results explain why the yield of 1,2-AMN, formed on the external acid sites, is lowest on BEA3p(3h). Compared to BEA2 and BEA3, the lowest rate of 2,6-AMN formation observed with BEA2p(3h), and in particular BEA3p(3h), could be explained by the diffusional limitation occurring inside the pores of the zeolites. Although the cyclohexane adsorption experiments show that the micropore volume is the same for BEA2, BEA2p(3h), BEA3 and BEAp(3h), it is possible that the passivation leads to a slight decrease in the pore opening which could have an important effect on the diffusion of large molecules such as 2MN and 2,6-AMN.

Figure 3A:
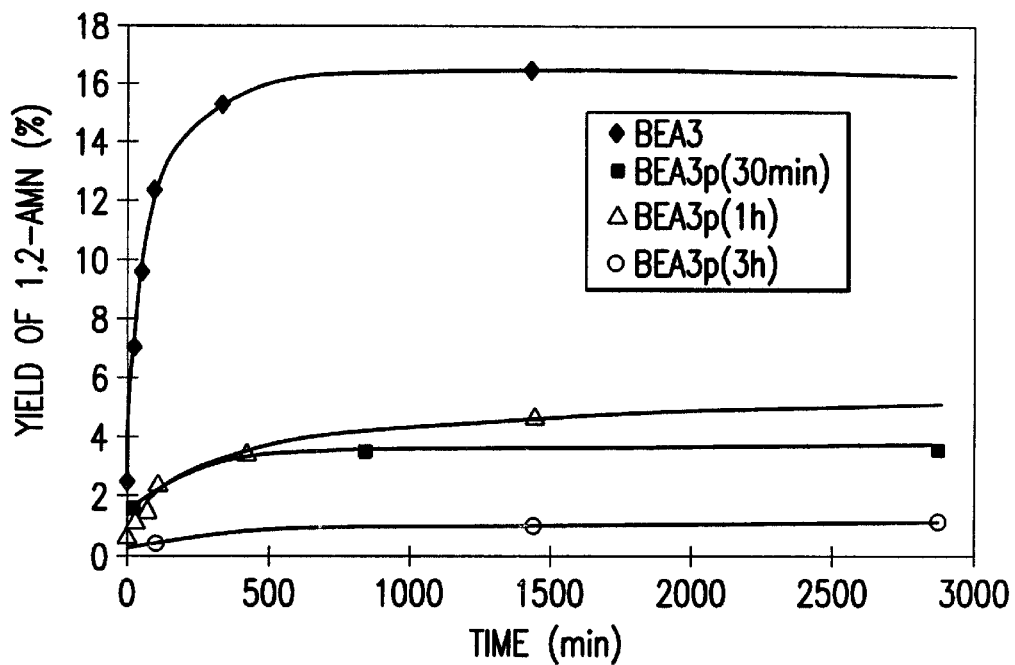
FIG. 3a shows the yield of 1,2-AMN versus reaction time over zeolite BEA3, BEA3P(30min)/BEA3p(1h)/and BEA3p (3h)
Figure 3B:
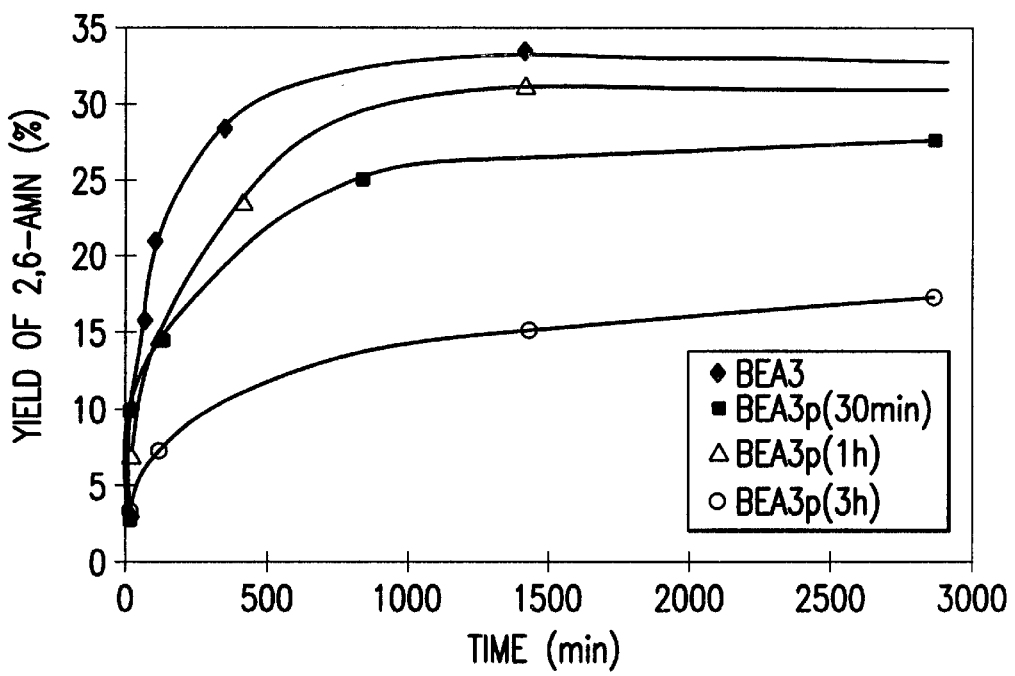
FIG. 3b shows the yield of 2,6-AMN versus reaction time over zeolite BEA3, BEA3P(30min), EEA3(1 h) and BEA3p(3 h)

In order to test further the effects of surface passivation, the time of coating, of the largest crystals (BEA3) was decreased from 3h to 1h (BEA3p(1h)) and 30min (BEA3p(30min)). FIGS. 3a and 3b show the yield of 1,2-AMN and 2,6-AMN, respectively, versus reaction time over zeolite BEA3, BEA3P(30 min), BEA3p(1h) and BEA3p(3h) using 0.10 g of catalyst at 100° C., wherein the ratio of 2MN to acetic anhydride is 1:1 and 1.1 mmol, in 0.860 mL of solvent. The conversions to 1,2-AMN and 2,6-AMN on BEA3p(3h), BEA3p(1h) and BEA3p(30min) are compared to those from BEA3 in FIG. 3b. The yield of 1,2-AMN is dramatically suppressed on the passivated zeolites, and in particular on BEA3p(3h) with the largest external surface covering. However, the yield of 2,6-AMN is significantly higher from BEA3p(30min) and BEA3p(1h) than from BEA3p(3h) and is likely due to enhance diffusional limitations as the thickness of the amorphous layer is increased. Upon reduction of surface acid sites, significant increases in the selectivity for 2,6-AMN occur. The amount of surfaces coating on the large crystals determines the yield of 2,6-AMN and the selectivity to this product.

Figure 4A:
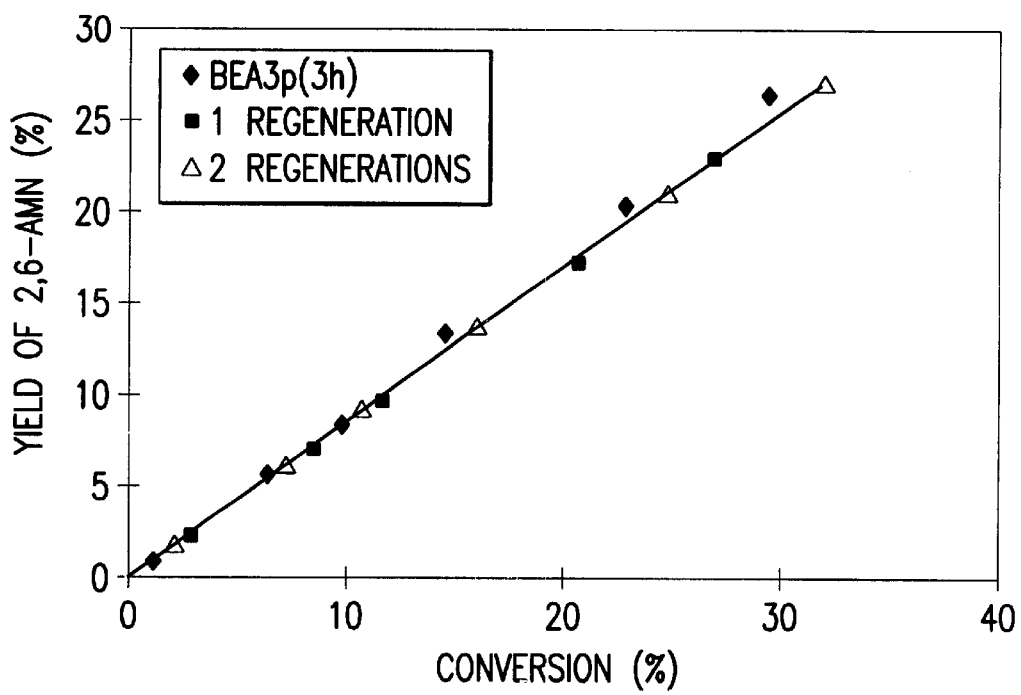
FIG. 4a shows the yield of 2,6-AMN versus total conversion over zeolite BEA3p(3 h) as function of number of regeneration.
Figure 4B:
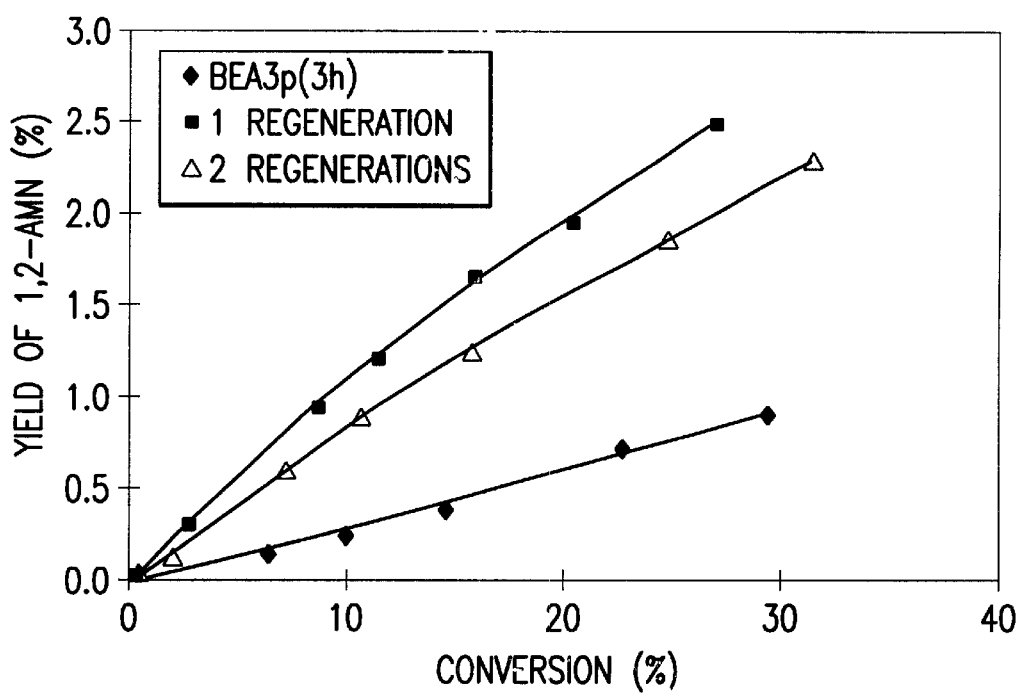
FIG. 4b shows the yield of 1,2-AMN versus total conversion over zeolite BEA3p(3 h) as function number of regeneration.

The regeneration of BEA3p(3h) was investigated. FIGS. 4a and 4b show the yield of 2,6-AMN and 1,2-AMN, respectively, versus total conversion over zeolite BEA3p (3h) as function of number of regeneration at 100° C., wherein the ratio of 2MN to acetic anhydride is 1:1. As can be seen from the data illustrated in FIG. 4a, the yield of 2,6-AMN is similar on the fresh zeolite and on the regenerated samples. However, an increase in the selectivity to 1,2-AMN occurs when the catalyst is regenerated, as seen in FIG. 4b. The selectivities to 1,2-AMN from the regenerated samples correspond to the values obtained on BEA3p(1h). This suggests that on the sample passivated 3h (BEA3p (3h)), the amorphous silica is sintering during regeneration and making available surface acid sites.

EXAMPLE 1

A synthetic protocol for a representative example of the acylation of a zeolite is as follows. Other zeolites are made analogously.

Preparation of Zeolite Beta

Numerous samples of zeolite beta with different Si/Al ratios and crystal sizes were used in this study for the acylation of 2MN. The sample denoted BEA1 was obtained from PQ and was ion exchanged with a 1.0 N $NH_4CL$ solution for 24h at ~80° C. (repeated 3 times) with subsequent calcination to 550° C. in air to generate the proton form. BEA2 and BEA3 were synthesized in fluoride media by modifying the method reported by Camblor, et al., J. Mat. Chem., 8, 12137 (1998), the contents of which are herein incorporated by reference. Tetraethylammonium fluoride (12.13 g, 81.3 miol, Aldrich) and aluminum nitrate nonohydrate (0.92 g, 2.45 mmol, Aldrich) were dissolved in water (13.58 g, 75.44 mmol). To this solution was added tetraethylorthosilicate (25.45 g, 122.2 mmol, Aldrich) dropwise with stirring. The solution was allowed to stir for 24h, after which the alcohol generated by hydrolysis was removed in vacuo. Additional water was added and the evaporation procedure was repeated. The gel obtained and 50 mg of zeolite beta seed crystals were transferred to a Teflon®-lined autoclave and heated under autogenous pressure at 140° C. for 7 days in rotary mode (BEA2) or in static mode (BEA3). The samples were recovered by filtration, washed with water and dried in air overnight at 100° C. The samples were calcined in air using the following temperature program: heat to 175° C. at 1°/min and hold at 175° C. for 2h, heat to 550° C. at 1°/min and hold at 550° C. for 6h.

EXAMPLE 2
Post-synthetic Modification of Zeolite Beta

Modifications of the zeolite beta crystals were performed using the following method: 0.25 g of HBEA (BEA1, BEA2 or BEA3) were stirred under argon atmosphere in 3 Ml of hexanes to which 0.1 Ml of TEOS was added. Stirring, was continued for 3h, 1h or 30min, after which the zeolite was recovered by filtration and washed with hexanes. This method has been shown to coat the surface of zeolite beta with silica. The samples are identified by the letter p followed by the time of coating, e.g., BEA1p(3h) denotes the BEA1 sample that was contacted with TEOS for 3h.

Characterization of Zeolite Beta

X-ray powder diffraction (XRD) patterns were collected on a Scintag XDS 2000 diffractometer using CuKα radiation. Nitrogen adsorption isotherms were obtained at 77K using an Omnisorp 100 sorption apparatus. Vapor phase cyclohexane isotherms were obtained on a McBain-Bakr balance. The micropore volume was determined at $P/P_0=0.25$. Prior to all adsorption experiments, the samples were degassed under vacuum at 250° C. for 2h. Scanning electron micrographs (SEM) were recorded on a Camscan Series 2-LV scanning electron microscope. X-ray photoelectron spectroscopy (XPS) experiments were performed on a Kratos AXIS-HS spectrometer. The X-ray source was monochromatized AlKα at 1478 Ev. Elemental analyses were performed by Galbraith Laboratories Inc., Knoxville, Tenn. The increase in weight of the used catalysts were obtained on a Dupont Instruments 951 Thermogravimetric Analyzer (TGA). The samples were heated in air to 800° C. and maintained 1h at 800° C. The extraction of the carbonaceous compounds deposited in the zeolite was carried out according to the procedure described by Guisnet and Magnoux, P., Appl. Catal. 54, 1 (1989), the contents of which are herein incorporated by reference.

EXAMPLE 3
Acylation Reaction

The following is a representative protocol for the acylation reaction in accordance with the principles of the invention. All chemicals were purchased from Aldrich Chemical Co. Only acetic anhydride has been purified (under reflux with magnesium for 5 days then distilled) before used.

Acylation reactions were carried out in a batch reactor under argon at 100° C. with acetic anhydride as the acylating reagent and 1,2-dichloroethane as solvent. Prior to use, 0.10 g or 0.25 g of catalyst were calcined in-situ under air to 550° C. 2MN, acetic anhydride (1.1 mmol) and an internal standard (1,3,5-tri-tert-butylbenzene or dodecane) were dissolved in 0.860 Ml of solvent and added to the vessel. Aliquots of the reaction mixture were sampled and analyzed by gas chromatography on a 30 m HP-5 column.

At the end of the reaction, the sample was recovered by filtration, washed with dichloromethane and dried at room temperature, in vacuo. Then the sample was regenerated under dried air to 550° C. or characterized by different methods.

Catalyst Testing

The external surface activity of the zeolite was measured using the conversion of the bulky allyl 3-5-di-tert-butylphenyl ether. This ether is too large to enter the pores of zeolite beta and is transformed into 2 allylphenol that is then cyclized into 2-methyldihydrobenzofuran:

SCHEME 2

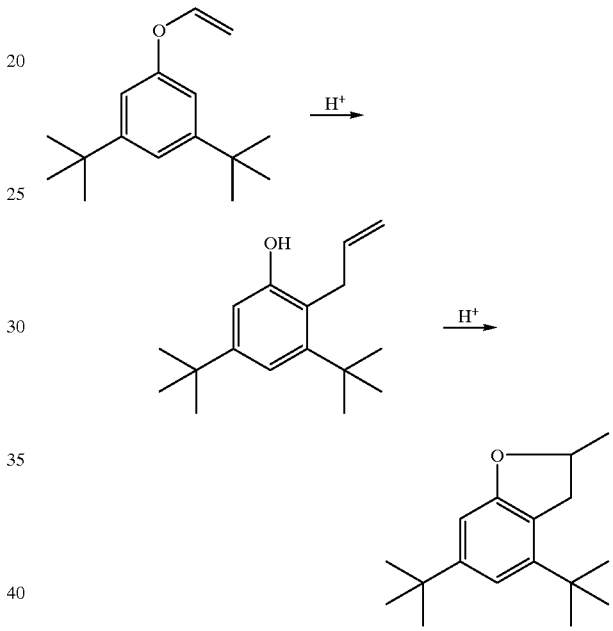

The reaction was carried out in a batch reactor under argon at 100° C. with 0.10 g of activated zeolite, 0.4 mmol of allyl 3-5-di-tert-butylphenyl ether and 2 Ml of 1,2-dichloroethane. Aliquots of the reaction mixture were sampled and analyzed by gas chromatography on a 30 m HP-5 column.

What is claimed is:

1. A process for shape selective acylation of an organic compound, the process comprising:
   a) reducing the number of surface acid sites without dealumination, no at least a portion of the surface of a zeolite without substantially reducing the number of internal acid sites; and
   b) acylating an organic compound in the presence of the zeolite.

2. The process of claim 1 wherein the zeolite is natural or synthetic.

3. The process of claim 1 wherein the zeolite is a zeolite with a unidimensional network.

4. The process of claim 3 wherein the zeolite is selected from the group consisting of zeolite ZSM-12, zeolite ZSM-22, zeolite ZSM-23, zeolite ZSM-48, VPI-8, VPI-5, SAPO-5, SAPO-11, SSZ-31, and theta-1.

5. The process of claim 1 wherein the zeolite is a zeolite with a multi-dimensional network.

6. The process of claim 5 wherein the zeolite is selected from the group consisting of zeolite beta, zeolite Y, zeolite X, zeolite ZSM-5, zeolite ZSM-4, zeolite L, zeolite ZSM-11, mordenite, ferrierite, SSZ-36, SSZ-35, gmelinite, NU-87, SAPO-34, Rho, zeolite A, CIT-1, SSZ-33, SSZ-26, SSZ-16, SSZ-13, zeolite ZSM-18, and zeolite HY.

7. The process of claim 1 wherein the acylation occurs in the presence of an acylating agent, wherein the acylating agent is selected from the group consisting of the halides of aliphatic carboxylic acids and the anhydrides of carboxylic acids.

8. The process of claim 7 wherein the acylation agent is selected from the group consisting of acetic anhydride, propanoic anhydride, isobutyric anhydride, trifluoroacetic anhydride, trichloroacetic anhydride, monochloroacetyl anhydride, dichloroacetyl anhydride, acetyl chloride, monochloroacetyl chloride, dichloroacetyl chloride, propanoyl chloride, isobutanoyl chloride, pivaloyl chloride, and crotonyl chloride.

9. The process of claim 1 wherein at least a portion of the surface of the zeolite is modified by surface poisoning or surface passivating.

10. The process of claim 9 wherein at least a portion of the surface of the zeolite is passivated by coating that portion of the surface with silica.

11. The process of claim 9 wherein the surface poisoning of the zeolite occurs in the presence of 2,4,6-tri-tert-butylpyridine or triphenylphosphine.

12. The process of claim 1 wherein the organic group is selected from the group consisting of olefins, aromatic hydrocarbons, phenolic compounds, and aromatic heterocyclic compounds, wherein the organic group is substituted or unsubstituted.

13. The process of claim 12 wherein the organic group is a single or multiple ring compound.

14. The process of claim 13 wherein the organic group is selected from the group consisting of toluene, 2-methoxynaphthalene and tetralin.

15. The process of claim 12 wherein the organic compound is phenol or anisole.

16. The process of claim 12 wherein the organic compound is selected from the group consisting of pyridine, pyrimidine, quinoline, isoquinoline, purine, pyrrole, thiazole, oxazole, pyrazole, imidazole, indole furan, benzofuran, thiophene and benzothiophene.

17. The process of claim 1 wherein the organic group is substituted with one or more moieties selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein the moiety is substituted or unsubstituted.

18. The process of claim 17 wherein the moiety substitution is selected from the group consisting of $C_1$–$C_5$ alkyl, $C_1$–$C_5$ alkoxy, and phenyl.

19. The process of claim 1 wherein the organic group is functionalized with a moiety selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

20. The process of claim 1 wherein the acylation is carried out in the presence of an optionally halogenated organic solvent.

21. The process of claim 20 wherein the solvent is an aliphatic or aromatic hydrocarbon, an aliphatic, cycloaliphatic or aromatic ether oxide, an aprotic polar solvent, a nitrated compound, an aliphatic or aromatic nitrile, a linear or cyclic carboxamide, dimethylsulphoxide, tetramethylenesulphone, or hexamethylphosphotriamide.

22. The process of claim 1 wherein the acylation occurs in the absence of a solvent.

23. A process for shape selective acylation of an aromatic hydrocarbon, the process comprising.

a) passivating at least a portion of the surface of a zeolite beta without substantially reducing the number of internal acid sites; and without dealumination, and b) acylating the aromatic hydrocarbon in the presence of the zeolite beta.

24. The process of claim 23 wherein the aromatic hydrocarbon is selected from the group consisting of toluene, 2-methoxynaphthalene, and tetralin.

25. The process of claim 9 wherein at least a portion of the surface of the zeolite is passivated by coating that portion of the zeolite with an agent selected from the group consisting of tetralkoxysilane, dimethyldichlorosilane, trimethylchlorosilane, tetramethyldisilazane, and hexamethyldisilazane.

26. The process of claim 25 wherein the agent is selected from the group consisting of tetramethoxysilane, tetraethoxysilane, and dimer to hexamer of tetraalkoxysilane.

* * * * *